(12) United States Patent
Niwa

(10) Patent No.: US 7,460,641 B2
(45) Date of Patent: Dec. 2, 2008

(54) X-RAY IMAGE TAKING DEVICE

(75) Inventor: Hiroaki Niwa, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 183 days.

(21) Appl. No.: 11/312,893

(22) Filed: Dec. 19, 2005

(65) Prior Publication Data

US 2006/0098775 A1     May 11, 2006

Related U.S. Application Data

(63) Continuation of application No. 10/703,853, filed on Nov. 7, 2003, now Pat. No. 6,977,988.

(30) Foreign Application Priority Data

Nov. 15, 2002    (JP)    ............................ 2002-332620

(51) Int. Cl.
    *H05G 1/10*     (2006.01)

(52) U.S. Cl. ....................................... 378/95; 378/98.8

(58) Field of Classification Search .................. 378/95, 378/96, 97, 98.8, 114, 115, 116; 250/370.08, 250/370.09
See application file for complete search history.

(56) References Cited

U.S. PATENT DOCUMENTS 6,516,098 B2 *   2/2003    Nonaka ...................... 382/274
6,977,988 B2 *  12/2005    Niwa ........................... 378/95

FOREIGN PATENT DOCUMENTS

JP            2002055164      2/2002

* cited by examiner

*Primary Examiner*—Courtney Thomas
(74) *Attorney, Agent, or Firm*—Morgan & Finnegan, LLP

(57) ABSTRACT

An X-ray detector for drive timing setting is provided outside an image taking region of a sensor unit. Thus, an X-ray image taking device is constructed such that a case structure is simple and a preferable image which is not affected by back-scattering can be captured.

1 Claim, 5 Drawing Sheets

X-RAY IMAGE TAKING DEVICE

RELATED APPLICATION INFORMATION

This application is a continuation of application Ser. No. 10/703,853, filed Nov. 7, 2003 now U.S. Pat. No. 6,977,988.

BACKGROUND OF THE INVENTION

1. Field of the Invention

The present invention relates to an X-ray image taking device that records an X-ray image.

2. Related Background Art

With respect to X-ray image taking for medical diagnosis, a film screen system in which an intensifying screen and an X-ray photograph film are combined is often used. According to this method, because an X-ray transmitted through an object includes internal information of the object, the internal information is converted into visible light proportional to an intensity of the X-ray by the intensifying screen to photosensitize the X-ray film, thereby forming an X-ray image on the X-ray film.

In recent years, a digital image taking device has been widely used for a general image taking region such as a chest, in which an image is taken using the X-ray film up to now. Accordingly, it is possible to capture a digital image in the field of diagnostic image.

A high resolution digital X-ray detector has been already proposed. This X-ray detector is composed of a two-dimensional array using 3000 to 4000 detection elements represented by photo diodes or the like in the respective dimensions. Each of the detection elements produces an electrical signal corresponding to a brightness of a pixel of an X-ray image projected to the detector. The electrical signal from each of the detection elements is separately read and converted into a digital signal. After that, an image process, a storing operation, and a display operation are conducted.

FIG. 2 is a schematic view showing a sectional structure of an image taking unit of a digital X-ray image taking device. As shown in FIG. 2, the image taking unit is composed of a phosphor 501 and a photoelectric conversion element 502, which are used in combination. With respect to the photoelectric conversion element 502, for example, an amorphous silicon film (a-Si film) is used as a photoelectric conversion layer.

The amorphous silicon film is suitable on the following points. That is, the amorphous silicon film can be formed on a large-size sensor substrate such as a glass substrate. In addition, the amorphous silicon film can be used as a semiconductor material for a TFT serving as a switching element. The X-ray incident into the digital X-ray image taking device is converted into visible light by the phosphor 501. Then, a photo carrier is produced by light absorbed in the semiconductor layer of the photoelectric conversion element 502 and stored therein.

In the digital X-ray image taking device, in addition to an X-ray detecting unit for capturing an image, another X-ray detecting unit is provided for setting an image taking drive timing. The X-ray detecting unit for setting the image taking drive timing is used to measure a period from an irradiation instruction issued to an X-ray generator to an actual X-ray irradiation (pre-delay period) or a period from the completion of the issue of the X-ray irradiation instruction to the completion of the actual X-ray irradiation (post-delay period).

These periods are varied according to a system structure of the X-ray image taking device and each X-ray generator. Therefore, it is necessary to measure the periods at the time of setting each system and to set drive timings.

It is necessary to set the pre-delay period in the case where the digital X-ray image taking device has a movable grid. Predetermined linear movement of the movable grid is required during the capture of an X-ray image. Therefore, a timing for starting the grid movement operation is adjusted in accordance with a set value of the pre-delay period.

It is necessary to set the post-delay period in order to capture a preferable X-ray image by reducing a crosstalk among sensor pixels. It is proposed in Japanese Patent Application Laid-Open No. 2002-055164 that image reading from the sensor pixels is started after a lapse of a predetermined time from the completion of the actual X-ray irradiation, so that a preferable X-ray image in which the crosstalk among the sensor pixels is reduced can be captured. A timing for starting image reading from the completion of the transmission of an X-ray irradiation instruction signal is adjusted in accordance with a set value of the post-delay period.

The X-ray detector for setting the image taking drive timing is located in the front or the rear of a sensor near the center of the image taking unit. This is because the X-ray detector has also a function as an X-ray monitor that detects a state of the X-ray irradiation each time image taking is performed.

However, in the case where the X-ray detector is located near the center of the image taking unit, a case structure of the image taking unit is complicated, which leads to an increased cost. In addition, a defect in which the X-ray detector and its attachment mechanism are reflected on an X-ray image is caused due to an adverse influence of a back-scattered radiation.

Up to now, in order to capture an image with a preferable image quality, it is necessary to minimize a charge accumulation time of the sensor. Therefore, it is required that the completion of the X-ray irradiation is detected each time image taking is performed. However, in recent years, a sensor capable of capturing a preferable image with a low noise even if a charge accumulation time which is not minimized is set has been developed. In particular, in the case of an X-ray image taking device in which a fixed charge accumulation time drive is employed, it is not essential to detect the completion of the X-ray irradiation each time image taking is performed.

SUMMARY OF THE INVENTION

Thus, the present invention has been made in view of the above-mentioned problems. An object of the present invention is to provide an X-ray image taking device in which an X-ray detector for setting an image taking drive timing is provided outside an image taking region of a sensor, so that a case structure is simple and a preferable image which is not affected by back-scattering can be captured.

According to the present invention, the foregoing object is attained by providing an X-ray image taking device, including:

an emitting unit that emits an X-ray;

a sensor that receives the X-ray on an image taking region thereof and converts the received X-ray into image data;

a drive unit that drives the sensor;

an X-ray detecting unit that sets a drive timing of the drive unit in accordance with a timing at which the X-ray emitted from the emitting unit is detected; and a control unit that controls the emitting unit, the drive unit, and the X-ray detecting unit, in which the X-ray detecting unit is provided outside the image taking region of the sensor.

Other objects, features and advantages of the present invention will be apparent from the following descriptions taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the descriptions, serve to explain the principle of the invention.

DETAILED DESCRIPTION OF THE PREFERRED EMBODIMENTS

A preferred embodiment of the present invention will be described in detail in accordance with the accompanying drawings.

Figure 1:
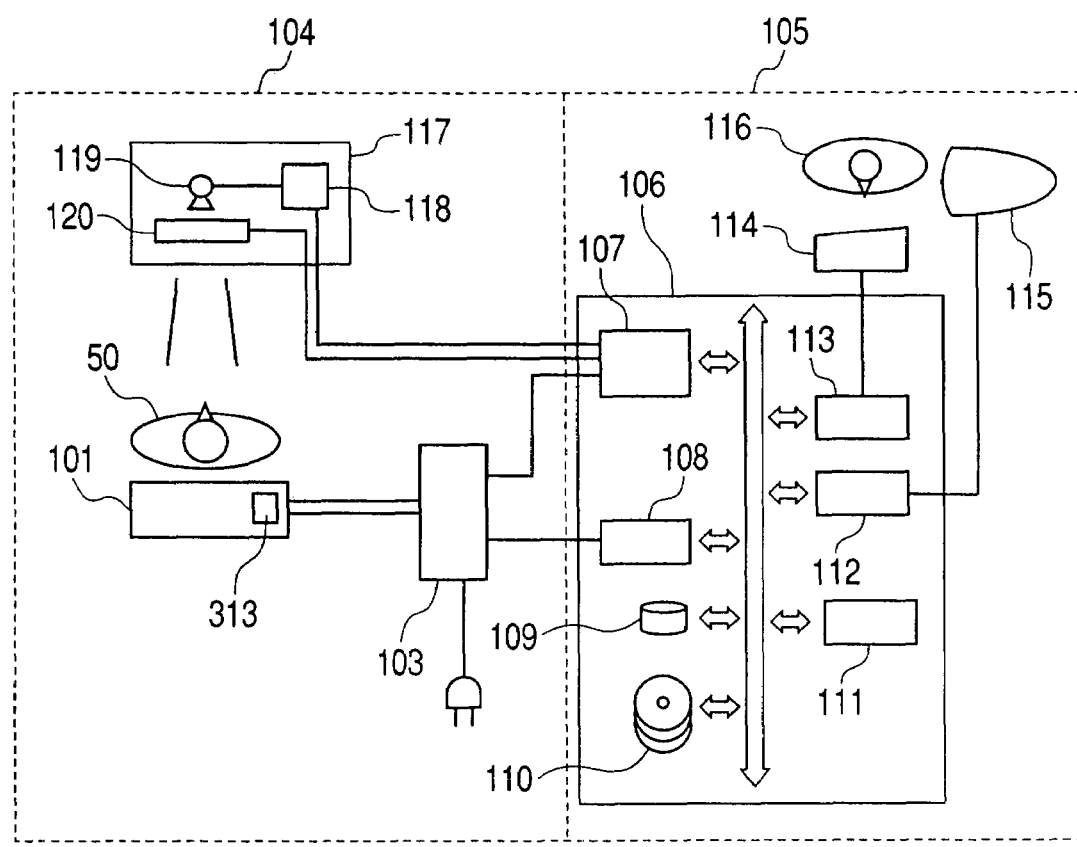
FIG. 1 is a schematic diagram showing an embodiment of an X-ray image taking system.
Figure 2:
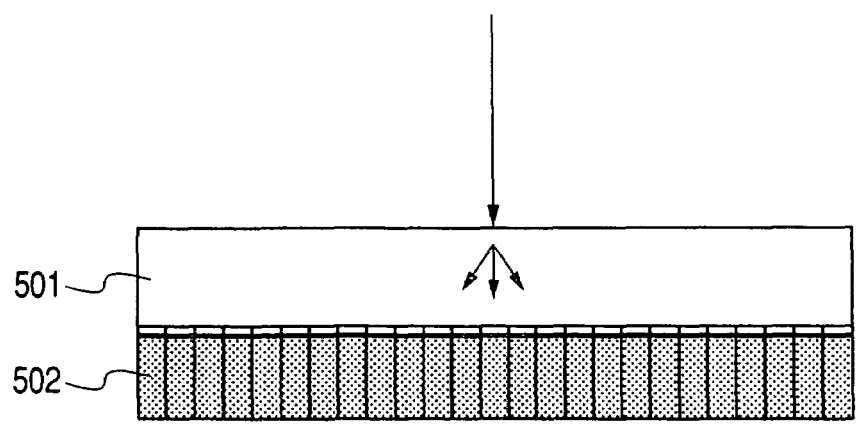
FIG. 2 shows an equivalent circuit of a first optical detection section.

FIG. 1 is a structural diagram of an X-ray image taking system. Reference numeral 104 denotes an X-ray room and 105 denotes an X-ray control room. An X-ray generator 117 that generates an X-ray is located in the X-ray room 104. The X-ray generator 117 is composed of an X-ray tube 119 that generates an X-ray, a high voltage generating source 118 which is controlled by an image taking controller 107 and drives the X-ray tube 119, and an X-ray aperture 120 that reduces an irradiation area of an X-ray beam generated by the X-ray tube 119 to a desirable image taking region.

A system controller 106 causes an internal RAM 111 to store image data obtained from an X-ray image taking device 101. The stored image data is subjected to adequate processes such as an offset correction and a gain correction. After that, according to an instruction of an operator 116, the processed image data is displayed on a display 115 or stored in a hard disk 109 or an external storage device 110.

The X-ray image taking device 101 is connected with the system controller 106 through a relay unit 103. A communication frame memory that temporarily stores an image signal obtained by image taking is mounted in the X-ray image taking device 101.

Power is supplied from an AC/DC power source provided in the relay unit 103 to the X-ray image taking device 101. The relay unit 103 has also a function in which in data communication between the X-ray image taking device 101 and the system controller (host computer) 106, a data format conversion (for example, conversion of an electrical signal to an optical signal or serial-parallel conversion) is conducted or an electrical insulation is conducted, for example.

Figure 3:
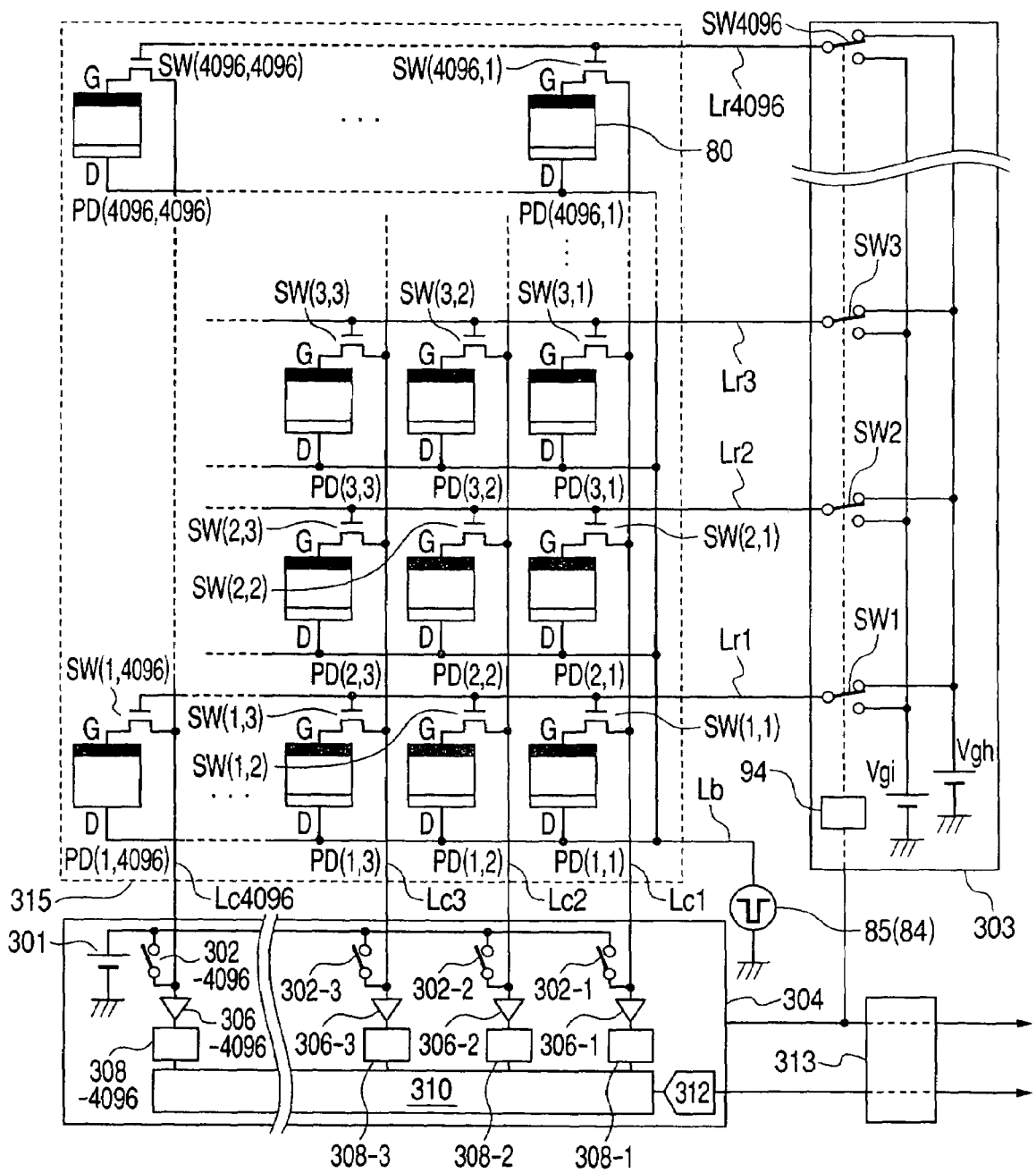
FIG. 3 is a diagram showing an array structural example of an optical detector.

FIG. 3 shows an equivalent circuit of an optical detector array including two-dimensionally arranged photoelectric conversion elements. An optical detector array 315 is composed of about 2000×2000 pixels to 4000×4000 pixels. An array area is about 200 mm×200 mm to 500 mm×500 mm.

In FIG. 3, the optical detector array 315 is composed of 2048×2048 pixels and the array area is 215 mm×215 mm. Therefore, a size of a pixel is about 105 μm×105 μm. In the case where 2048 pixels arranged in a transverse direction are assumed to constitute a block, the 2048 blocks are arranged in a longitudinal direction to achieve a two-dimensional structure.

In the optical detector array 315 shown in FIG. 3, the 2048×2048 pixels are divided into 2048 columns by column signal lines Lc1 to Lc2048. Signal charges in the 2048 pixels are simultaneously read for each row and transmitted to an analog multiplexer 310 through the respective column signal lines Lc1 to Lc2048, preamplifiers 306-1 to 306-2048, and S/H circuits 308-1 to 308-2048. Here, time axis multiplexing is conducted and then the signal charges are converted into digital signals by an A/D converter 312 in succession.

Figure 4:
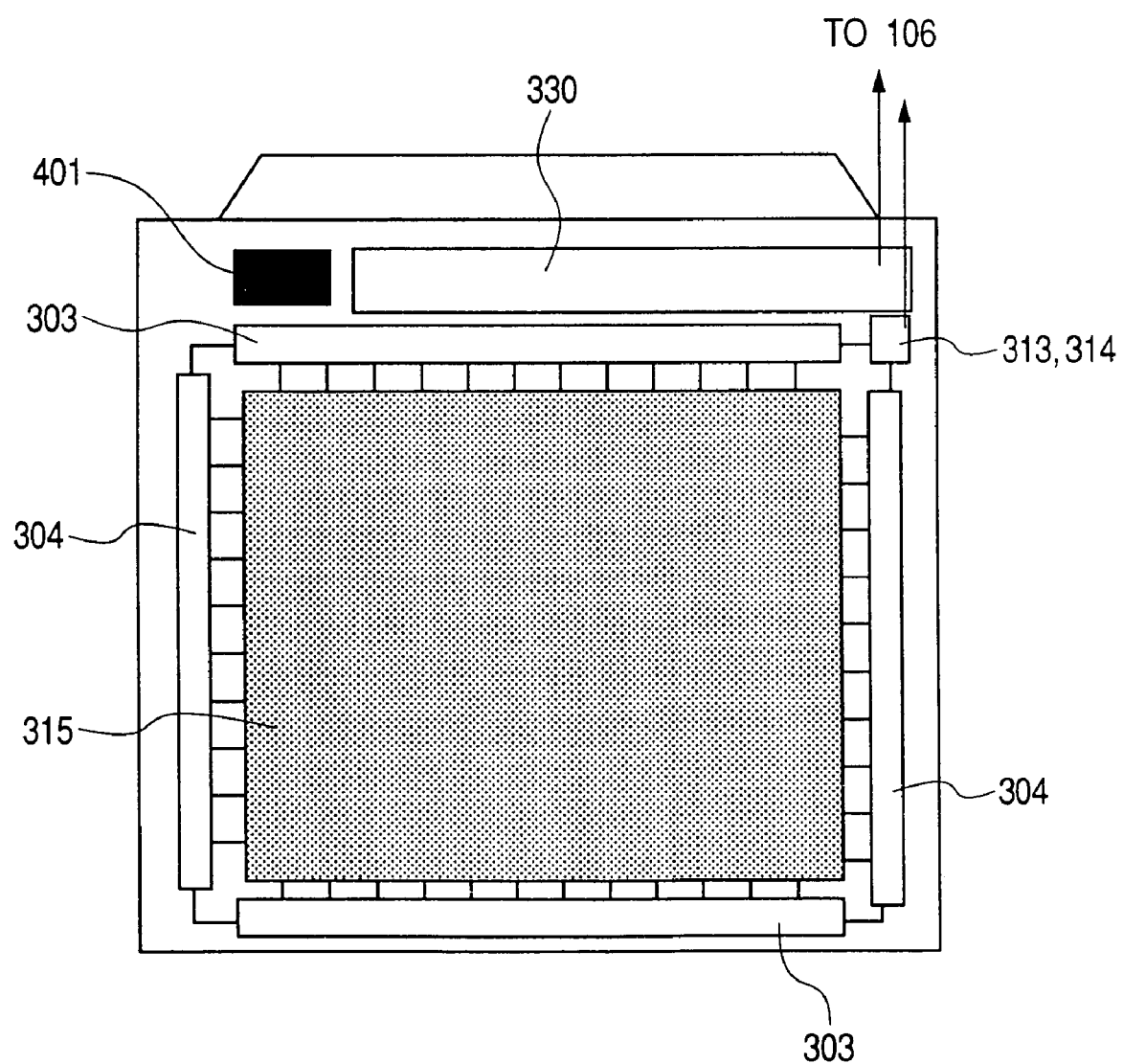
FIG. 4 is a structural view showing an image taking device of the present invention.

FIG. 4 shows a structure of the X-ray image taking device. The optical detector array 315 is located near the center of the X-ray image taking device. Gate driving circuits 303, signal reading circuits 304, a driver 313, a communication frame memory 314, a power source 330, and the like are arranged in an available space of the X-ray image taking device case.

An X-ray detector 401 for drive timing adjustment is located in a space outside the detection region of the optical detector array 315. The X-ray detector 401 is composed of a phosphor that converts an X-ray into visible light and a visible light sensor that detects the visible light.

The visible light sensor is selected from an amorphous silicon sensor, a photo transistor, a photo diode, and the like. In the selection, a dark current characteristic and an optical response characteristic become important factors. The drive timing adjustment will be described later in detail.

Figure 7:
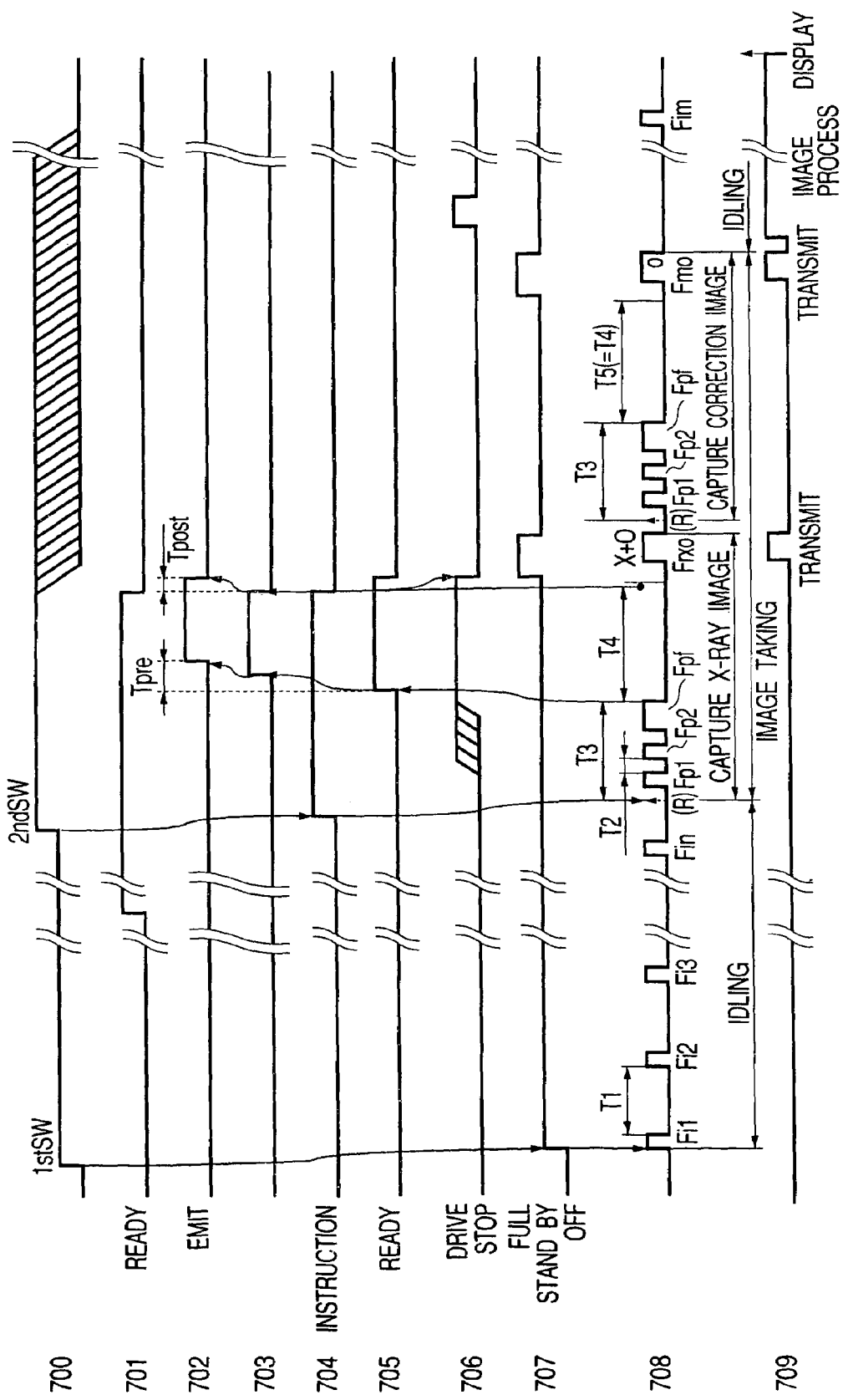
FIG. 7 is a timing chart of the X-ray image taking system according to the embodiment of the present invention.

FIG. 7 is a timing chart from a time when the X-ray image taking is started to a time when an image is captured. Note that fixed accumulation image taking in which the charge accumulation time of the sensor is fixed will be described in this embodiment.

In FIG. 7, reference numeral 700 denotes an image taking instruction signal to an operator interface 114; 701, a ready signal of the X-ray generator 117; 702, an actual X-ray irradiation state; 703, an X-ray irradiation instruction signal to the X-ray generator 117; and 704, an image taking instruction signal transmitted from the image taking controller 107 to the driver 313 based on an instruction of the operator 116. In addition, reference numeral 705 denotes an image taking ready signal of the X-ray image taking device 101; 706, a drive signal of a grid; 707, a power control signal in the X-ray image taking device 101; 708, a drive state of the X-ray image taking device 101 (particularly, reading operation of the charges from the optical detector array 315); and 709, a transfer of an image and the like. When the operator interface 114 of the operator 116 receives a command of an image taking preparation instruction (1stSW in 700), the image taking controller 107 outputs a command for transition of a state of the X-ray generator 117 to an image taking ready state and a command for shifting a state of the X-ray image taking device 101 to an image taking preparation state.

When the command is received, the driver 313 applies a bias to the optical detector array 315 and repeats (refreshing and) idle-reading Fi. The instruction command is, for example, a command from the 1st switch for the irradiation instruction SW to the X-ray generator (generally, rotor-up of the tube and the like are started) or a command for starting the preparation of the X-ray image taking device 1101 in the case where a predetermined time (several seconds or more) is required for the image taking preparation of the X-ray image taking device 101.

In this case, it is unnecessary that the operator 116 actively issues to the X-ray image taking device 101 an image taking preparation instruction command. That is, when patient information, image taking information, and the like are inputted to the operator interface 114, the inputted information may be read as the image taking device preparation instruction command by the image taking controller 107 to shift the state of the X-ray image taking device 101 to the image taking device preparation state.

In the image taking device preparation state, in order to prevent a capacitor from being kept in a saturated state, which results from a dark current gradually accumulated in an optical detection section after idle-reading in a photoelectric conversion mode, (refreshing R and) the idle-reading Fi are repeated at given intervals.

Next, when the operator 116 issues to the operator interface 114 an image taking instruction command (700: 2ndSW), the image taking controller 107 controls an image taking operation while the X-ray generator 117 and the X-ray image taking device 101 are synchronized with each other. In accordance with the image taking instruction command (700: 2ndSW), an image taking instruction signal is asserted to the X-ray image taking device 101 at a timing as indicated by using the X-ray irradiation instruction signal 703. The driver conducts predetermined image taking preparation sequence drive as indicated in the image taking drive state 708 in response to the image taking instruction signal.

More specifically, in the case where refreshing is necessary, refreshing is conducted. Then, a specific idle-reading Fp for an image taking preparation sequence is conducted predetermined times and a specific idle-reading Fpf for a charge accumulation state is conducted to transit to the charge accumulation state (image taking window: T4). At this time, the number of times the idle-reading Fp for the image taking sequence is performed and a time interval T2 are set in advance by the image taking controller 107 before the image taking instruction.

It is practically necessary that a required period (T3) from the irradiation instruction to the completion of the image taking preparation is short. Therefore, the specific idle-reading Fp for the image taking preparation sequence is conducted. Further, when the irradiation instruction is generated in any of idling drive states, the image taking preparation sequence drive immediately starts, so that the period (T3) from the irradiation instruction to the completion of the image taking preparation is shortened to improve an operability.

When the image taking preparation of the X-ray image taking device 101 is completed, the driver 313 sends the ready signal 705 of the X-ray image taking device to the image taking controller 107 in reply thereto. The image taking controller 107 asserts the X-ray irradiation instruction signal 703 in accordance with the transition of the image taking ready signal 705. The X-ray generator 117 emits an X-ray while the X-ray irradiation instruction signal 703 is asserted.

The driver 313 starts to move the grid in synchronization with the image taking preparation of the optical detector array 315. This is because the image taking is conducted in a state in which the grid is suitably moved in synchronization with the actual X-ray irradiation state 702. In this case, it is necessary to operate the driver 313 at a suitable grid movement start timing which is set by the image taking controller 107.

When the predetermined amount of X-ray is generated, the image taking controller 107 negates the X-ray irradiation instruction signal 703. In accordance with a timing of negating the signal, the driver 313 immediately stops the grid.

The X-ray image taking device 101 starts the operation of the signal reading circuits 304 which are still in a standby state after a lapse of a predetermined period (T4).

In general, the period T4 is longer than a period for which the X-ray is actually emitted. However, there is the case where the period for which the X-ray is actually emitted is substantially equal to or longer than the period T4 depending on image taking situations. In such a case, the image taking controller 107 negates the X-ray irradiation instruction signal to complete the X-ray irradiation. After a lapse of a predetermined wait period for the setting of the signal reading circuits, image data is read from the X-ray detector array 315 by the driver 313 and transferred as a raw image to an image processor 108. When the transfer is completed, the driver 313 causes the signal reading circuits to transit to the standby state again.

Subsequently, the X-ray image taking device 101 captures a correction image. That is, the image taking sequence for the previous image taking is repeated to capture a dark image with no X-ray irradiation and the dark image for correction is transferred to the image processor 108. In this case, there is a fear that an X-ray irradiation time and the like in the image taking sequence are slightly changed for each image taking. However, in the case where the completely identical image taking sequence in which slight changes in X-ray irradiation time and the like are taken into account is reproduced to obtain the dark image, a higher quality image is captured. Note that the operation of the grid is not limited to the above description and the grid is stopped in the case where the dark image is obtained. After the dark image is obtained, an operation for initializing the grid is conducted.

In the actual system, there are a period from the assertion of the image taking ready signal 705 of the X-ray image taking device 101 to the start of the actual X-ray irradiation (pre-delay period: Tpre) and a period from the negation of the X-ray irradiation instruction signal 703 to the completion of the actual X-ray irradiation (post-delay period: Tpost). These periods are varied according to each system structure of the X-ray image taking device and each X-ray generator.

As described above, in order to accurately control the operation start timing of the movable grid and to capture a preferable image with less crosstalk by controlling an image reading timing, it is necessary to accurately set the pre-delay period and post-delay period.

Therefore, when the system is set, the pre-delay period and post-delay period are measured using the X-ray detector 401 for drive timing adjustment. The output of the X-ray detector 401 for drive timing adjustment is inputted to an AD port of a microcomputer mounted on the image taking controller 107 through an amplifier for amplification and the like. The respective periods are measured by the operation of the microcomputer.

In actuality, X-lay image taking is successively conducted on the X-lay detector 401 about ten times under an irradiation condition in which a sufficient output of the X-ray detector 401 is obtained. A time difference between the timing of the assertion of the image taking ready signal of the X-ray image taking device 101 and a timing at which the X-ray detector 401 detects the X-ray (=timing of actual X-ray irradiation) and a time difference between the timing of the completion of the X-ray irradiation instruction and the timing at which the X-ray detector 401 detects the X-ray are measured and the respective periods are calculated from respective measured average values.

According to the present invention, as described above, the X-ray detector 401 for drive timing adjustment is located outside the detection region of the optical detector array 315.

For example, in the case where it is desired to monitor an X-ray irradiation state each time image taking is performed, the X-ray detector 401 is located in the front or the rear of the optical detector array 315 and the measurement for drive timing is conducted using the X-ray detector in the setting of the system.

However, in the case where the X-ray detector 401 is located in the front or the rear of the optical detector array 315, because of the location thereof, a case mechanism is complicated and a space for the location is required. This location becomes a large negative effect in the case where it is desired to thin the case of the X-ray image taking device. In addition, the complicated mechanism leads to the increased cost.

In addition to this, because the X-ray detector 401 having an X-ray transmittance different from that in the optical detector array 315 is located within the detection region of the optical detector array 315, the location causes a defect in which the X-ray detector 401 is reflected on an image by the adverse influence of X-ray back-scattering.

In the X-ray image taking device in which the fixed charge accumulation time drive is particularly employed as in this embodiment, it is unnecessary to detect the completion of the X-ray irradiation each time image taking is performed. In addition, there is an X-ray generator that negates the ready signal 701 of the X-ray generator 117 at the completion of the irradiation. Even in a system using such an X-ray generator, it is unnecessary to detect the completion of the X-ray irradiation by using the X-ray detector.

For the purpose of drive timing adjustment, it is unnecessary to locate the X-ray detector in the front or the rear of the optical detector array. Thus, as described above, in the case where the X-ray detector is located outside the detection region of the X-ray detector array, the case structure can be simplified and a preferable image which is not affected by back-scattering can be provided.

Next, another embodiment of the present invention will be described.

Figure 5:
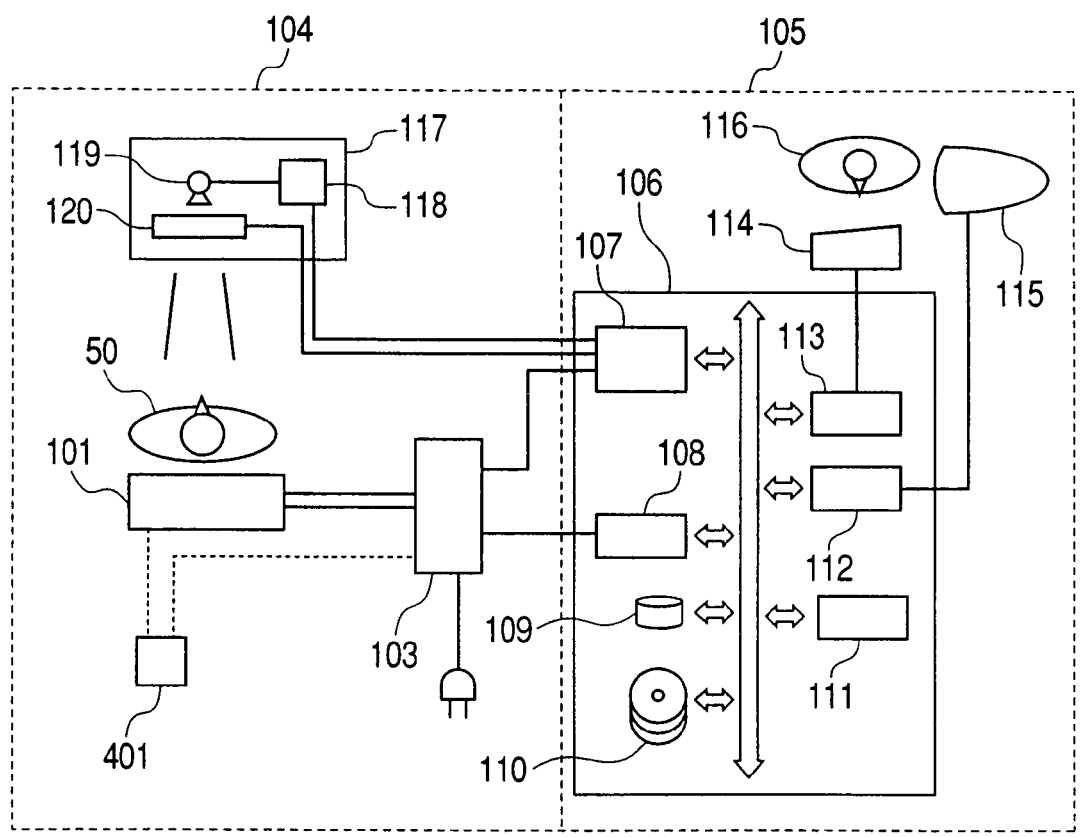
FIG. 5 is a diagram showing another embodiment of the X-ray image taking system of the present invention.

As shown in FIG. 5, a mechanism which can be connected with an external X-ray detector is provided in the X-ray image taking device 101 and thus it is constructed such that the X-ray detector can be connected with the mechanism if necessary. As described above, the pre-delay period and the post-delay period may be measured at the time of setting the system. Therefore, for the purpose of the measurement, it is unnecessary to locate the X-ray detector in the case of the X-ray image taking device 101.

Also, the phosphor and the amorphous silicon sensor which compose the X-ray detector are generally expensive. Accordingly, in the case where the X-ray detector is used as a tool, a reduction in cost of the X-ray image taking device itself can be realized. In addition, it is advantageous in aiming at reducing the weight of the X-ray image taking device.

Next, another embodiment of the present invention will be described.

Similarly, as shown in FIG. 5, a mechanism which can be connected with an external X-ray detector is provided in the relay unit 103 located between the X-ray image taking device 101 and the system controller 106 and thus it is constructed such that the X-ray detector can be connected with the mechanism if necessary.

The relay unit 103 is generally located in the X-ray image taking room. Therefore, in the case where the X-ray detector is connected with the relay unit 103, timing measurement can be easily conducted in the X-ray image taking room. Also, in this case, the pre-delay period and the post-delay period are measured by the microcomputer. A High/Low signal indicating whether or not an X-ray detection value exceeds a threshold value may be transmitted back to the microcomputer.

It is required that the X-ray image taking device 101 has an airtight structure in view of operability and safety. According to this embodiment, the airtight structure of the image taking unit can be further realized while the above-mentioned effects are kept.

Figure 6:
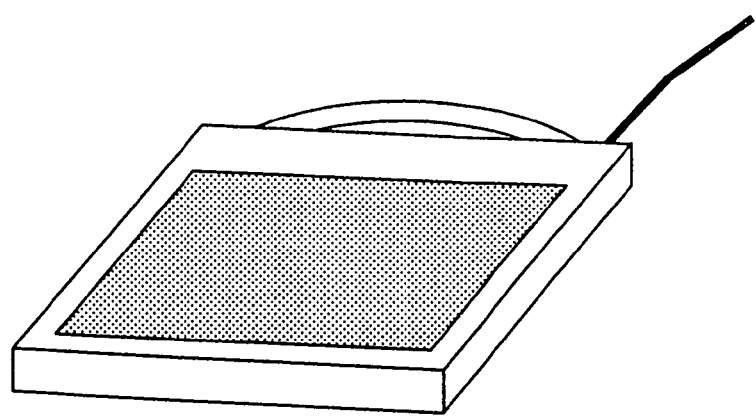
FIG. 6 shows an outline example of an electronic cassette.

Note that the X-ray image taking device may be constructed as in an electronic cassette. The electronic cassette has, for example, a thin case structure as shown in FIG. 6 and indicates a portable X-ray image taking device. In this case, the present invention is particularly effective in the case of aiming at thinning the case of the X-ray image taking device, reducing the weight thereof, and keeping the airtightness.

As described above, according to the present invention, there is provided the following effect. That is, there can be provided an X-ray image taking device which includes an emitting unit that emits an X-ray, a sensor unit that detects an X-ray image from an object so as to capture a two-dimensional flat image, and a control unit that controls image taking of the X-ray image taking device, in which an X-ray detector for drive timing setting is provided outside an image taking region of the sensor unit, whereby a case structure is simple and a preferable image which is not affected by back-scattering can be captured.

Note that the present invention may be applied to either a system constituted by a plurality of apparatuses (e.g., image processing apparatuses, interfaces, radiographic apparatuses, X-ray generation apparatuses, and the like) or an arrangement that integrates an image processing apparatus and a radiographic apparatus, or the like.

The present invention is not limited to the above embodiments and various changes and modifications can be made within the spirit and scope of the present invention. Therefore to apprise the public of the scope of the present invention, the following claims are made.

What is claimed is:

1. An X-ray image taking system, comprising:
   an X-ray image taking device including a sensor that receives an X-ray on an image taking region thereof and converts the received X-ray into image data;
   an X-ray detecting unit that receives the X-ray and transmits a signal in accordance with the reception of an X-ray, and is configured for separating the X-ray detecting unit from the X-ray image taking device and for being provided outside the image taking region of the sensor;
   a driving unit for moving the image taking device;
   a control unit that receives the signal transmitted from the X-ray detecting unit, and transmits a stop instruction signal to the drive unit so as to stop a movement of the image taking device, on the basis of a timing when a charge accumulation operation executed on the sensor completes and a post-delay period which is measured in advance,
   wherein the control unit sets the post-delay period to a period from a time when an X-ray irradiation operation is negated and a time when the control unit ends the reception of the signal transmitted from the X-ray detecting unit; and
   a connecting mechanism that externally connects the X-ray detecting unit with the X-ray image taking device.

* * * * *